United States Patent [19]

Gago et al.

[11] 4,344,979

[45] Aug. 17, 1982

[54] PROCESS FOR THE PREPARATION OF COATED SEEDS

[75] Inventors: Ignace Gago, Braine-l'Alleud; Guillaume Coppens, Brussels, both of Belgium

[73] Assignee: Interox (Societe Anonyme), Brussels, Belgium

[21] Appl. No.: 136,268

[22] Filed: Apr. 1, 1980

[51] Int. Cl.$^3$ .................................................. A01C 1/06
[52] U.S. Cl. .......................................... 427/4; 47/57.6; 71/77
[58] Field of Search ................... 427/4; 47/57.6; 71/77

[56] References Cited

U.S. PATENT DOCUMENTS

| | | | |
|---|---|---|---|
| 2,006,967 | 7/1935 | Sparks | 47/58 |
| 3,600,830 | 8/1971 | Hamilin | 427/4 |
| 3,698,133 | 10/1972 | Schreiber | 427/4 |
| 3,803,761 | 4/1974 | Watts | 427/4 |

FOREIGN PATENT DOCUMENTS 52-21164  2/1977  Japan .................................... 71/72

*Primary Examiner*—Sam Silverberg
*Attorney, Agent, or Firm*—Spencer & Kaye

[57] ABSTRACT

A process for the preparation of coated seeds, in which the seeds are initially treated with an aqueous phase. The treated seeds are then coated with a coating agent containing a peroxide compound and a hydrophilic polymer, and the coated seeds are dried.

21 Claims, No Drawings

PROCESS FOR THE PREPARATION OF COATED SEEDS

BACKGROUND OF THE INVENTION

The present invention relates to a process for the preparation of coated seeds.

The majority of cultivation methods give a very uncertain yield. Thus, if the seeds are sown directly in the fields, premature germination takes place before the average ambient humidity is sufficient to ensure the normal growth of the young plants, and this causes significant reductions in the yields. This phenomenon is particularly pronounced in the case of poorly protected seeds, in particular those having an exposed germ.

In order to improve the yield, it is possible to resort to transplanting techniques. In this case, vigorous and well-developed young plants are used and provision is made for the longest possible growth times. To achieve these objectives, the seeds are sown prematurely and the optimum conditions of temperature and humidity level, making it possible to obtain rapid and concomitant germination of the seeds, are selected. However, these techniques are generally uneconomic and only rarely enable quantitative yields to be obtained, either because the seeds do not germinate or because some of the seeds germinate late.

Furthermore, during storage of the seeds, significant losses occur which are generally due to an excessively high ambient humidity or to poor aeration of the silos.

A known technique for improving the germination levels of certain seeds, or for giving them a shape and dimensions suitable for mechanical sowing, consists in coating them with various types of coating agents. Thus, in order to improve the germinating ability of beetroot seeds (Belgian Pat. No. 859,566, filed on Oct. 11, 1977 in the name of the Applicant Company), it has been proposed to incorporate calcium peroxide in the coating agent. This technique, which has proved effective, cannot be directly applied to other seeds of uniform shapes, in particular because the coating agent does not adhere adequately to the seed.

This lack of adhesion is particularly pronounced in the case of poorly protected seeds.

In fact, during coating, a substantial swelling of certain seeds, due to the absorption of water, is frequently observed. After drying, the seed contracts and returns to its initial size, whereas the coating agent does not generally contract in the same proportions; therefore, it does not adhere adequately to the seed and it becomes fragile or splits off. In certain cases, it is difficult correctly to dry the seed under the layer of coating agent, and this entails risks of degradation during storage. These effects are particularly pronounced when the seeds used are leguminosae, maize and cruciferae seeds. Moreover, some coating agents, which on the whole possess valuable properties, can have secondary phytotoxic effects on certain seeds. Finally, in certain cases, it is difficult to coat the seeds in a uniform manner because their surfaces are uneven and do not permit uniform attachment of the coating agents.

SUMMARY OF THE INVENTION

The object of the present invention is to provide a process for the preparation of coated seeds, which does not exhibit the disadvantages of the known processes. This process makes it possible to improve the adhesion of the coating agent to the seeds and its strength, to prevent the inopportune swelling of the seeds during coating, to protect the seeds from the secondary phytotoxic effects of certain coating agents, to prevent premature germination of the seeds and to improve the storage stability of the coated seeds.

The invention further leads to a substantial additional improvement in the germination level of the seeds, to a reduction in the time required for emergence of the germs, and to a fungicidal and disinfecting action.

For this purpose, the present invention relates to a process for the preparation of coated seeds, in accordance with which the seeds are treated with an aqueous phase, the seeds treated in this way are coated with a coating agent containing a peroxide compound and a hydrophillic polymer, and the coated seeds thus obtained are dried.

DETAILED DESCRIPTION OF THE INVENTION

All types of organic or inorganic peroxide compounds can be used in the seed-coating agent according to the invention. The organic peroxide compounds which can be used include compounds such as benzoyl peroxide and its halogen derivatives, alkyl perbenzoates, such as tert.-butyl perbenzoate, p-menthane hydroperoxide, and also hydrogen peroxide addition products such as urea peroxide. The inorganic peroxide compounds are generally chosen from amongst per-salts such as alkali metal or alkaline earth metal perborates, percarbonates, persulphates and perphosphates and metal peroxides. Most frequently, inorganic peroxide compounds such as metal peroxides, more particularly alkaline earth metal peroxides, are preferably used. Very good results have been obtained by using calcium peroxide or magnesium peroxide.

The amount of peroxide compound present in the coating agent can vary within wide limits. It is generally between 0.1 and 99% of the total weight of the coating agent. Most frequently, the coating agent contains from 1 to 90% by weight of peroxide compound. Good results have been obtained with coating agents containing from 10 to 80% by weight of peroxide compound.

Various types of hydrophilic polymers can be used in the coating agent according to the invention.

The term hydrophilic polymer is understood as denoting all the polymeric organic compounds which essentially comprise monomeric units containing hydrophilic groups.

The hydrophilic polymers present in the coating agent are generally chosen from amongst polymers which possess a main chain containing carbon atoms which are directly or indirectly substituted by at least one hydroxyl group, —OH, carboxyl group, —COO—, or carbamyl group, —CON<. They can additionally be substituted by one or more further substituents such as halogen atoms or hydrocarbon groups. The main chain of the polymer can contain certain hetero-atoms such as oxygen and nitrogen. Good results are obtained with polymers in which the main chain essentially consists of carbon atoms and, if appropriate, oxygen atoms.

The hydrophilic polymers can be substituted by hydroxyl groups, —OH. Thus, polymers derived from substituted or unsubstituted aldoses can be used as adhesives. Cellulose, starch and their substitution derivatives can also be used. Good results have been obtained with alkylhydroxyalkylcelluloses such as methylhydroxyethylcelluloses and methylhydroxypropylcelluloses.

Other cellulose derivatives, such as methylcelluloses and carboxymethylcelluloses, are also suitable.

Advantageously, the hydrophilic polymers used according to the invention can be directly or indirectly substituted by carboxyl groups, —COO—, or carbamyl groups, —CON<. They can thus be substituted by groups $R_1$—COO—, —COO—$R_2$, —CON$R_3R_4$,

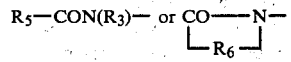

or alkyl chains —$R_7$—, the latter themselves being substituted by one or more of these groups, in which groups and chains $R_1$ and $R_5$ represent an optionally substituted hydrocarbon group containing from 1 to 6 carbon atoms, $R_2$ represents a hydrogen atom or an alkali metal atom, such as sodium or potassium, an alkaline earth metal atom, such as calcium or magnesium, an ammonium group or a group such as $R_1$, $R_3$ and $R_4$ represent a hydrogen atom or a group such as $R_1$, $R_6$ represents a carbon chain containing 3 or 4 carbon atoms and $R_7$ represents an alkyl chain containing from 1 to 40 carbon atoms.

The hydrophilic polymers used according to the invention can thus advantageously be substituted by one or more groups chosen from amongst the following groups: —O—CO—CH$_3$, —COOM, in which M represents a hydrogen atom, an alkali metal atom, such as sodium or potassium, an alkaline earth metal atom, such as magnesium or calcium, or an ammonium group, —COO—(CH$_2$)$_n$—H, in which n is an integer from 1 to 3,

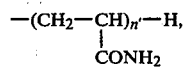

in which n' is an integer from 1 to 10,

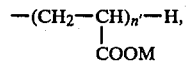

in which n' is an integer from 1 to 10 and M has the same meaning as above, and

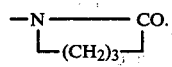

The main chain of the hydrophilic polymers used according to the invention can contain oxygen atoms. In this case, the polymers are advantageously chosen from amongst the derivatives substituted by carboxyl or carbamyl groups, such as the cellulose, alkylcellulose and starch derivatives defined above.

Good results have been obtained with the hydrolysed products resulting from the grafting of acrylonitrile onto starch, which products are also referred to as superabsorbents, such as those described in U.S. Pat. No. 3,935,099, filed on Apr. 3, 1974 and assigned to the U.S. Secretary of Agriculture.

It is possible for the hydrophilic polymers present in the coating agent not to contain heteroatoms in their main chain. In this case, it is possible for them not to contain substituents other than carboxyl or carbamyl groups. They can then be chosen, in particular, from amongst the homopolymers and copolymers of vinylpyrrolidone, of vinyl esters and of acrylic acid, and of derivatives of the latter, such as its salts and its esters, more particularly the sodium salts and the esters of C$_1$-C$_3$ aliphatic alcohols. Good results have been obtained with polyvinylpyrrolidone, polyvinyl acetate and poly-(sodium acrylate). The best results have been obtained with polyvinylpyrrolidone.

A composition of hydrophilic polymers containing both hydroxyl groups, —OH, and carboxyl groups, —COO—, or carbamyl groups, —CON<, can advantageously be used.

Thus, a mixture of polymers substituted by hydroxyl groups, —OH, with polymers substituted by carboxyl groups, —COO—, can advantageously be used. Good results have thus been obtained by using mixtures of totally or partially hydrolysed polyvinyl esters with carboxylated polymers such as polyacrylates. Such mixtures advantageously contain the ester and the carboxylated polymer in a weight ratio of between 10:1 and 1:10.

The hydrophilic polymers of the invention which are substituted by carboxyl and carbamyl groups can also advantageously be simultaneously substituted by hydroxyl groups. Amongst these particular polymers, hydroxycarboxylated polymers are particularly suitable.

The hydroxycarboxylated polymers are generally chosen from amongst partially hydrolysed polyvinyl esters, such as polyvinyl acetates, in which less than 90%, and preferably from 40 to 90%, of the ester groups are hydrolysed, and polymers containing carbon atoms which are substituted by both hydroxyl and carboxyl groups.

Particularly suitable hydroxycarboxylated polymers are those which contain monomeric units of the formula

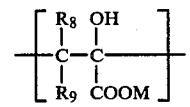

in which $R_8$ and $R_9$ represent hydrogen or an alkyl group containing from 1 to 3 carbon atoms which can be substituted by a hydroxyl group or by a halogen atom, it being possible for $R_8$ and $R_9$ to be identical or different, and in which M has the same meaning as above. The polymers of this type which are preferably used according to the invention are those polymers, as defined above, in which $R_8$ and $R_9$ represent hydrogen or a methyl group, it being possible for $R_8$ and $R_9$ to be identical or different. The best results have been obtained with the polymers in which $R_8$ and $R_9$ represent hydrogen. The polymers of this type are homopolymers or copolymers containing units, as defined above, of the same type or of several different types. If copolymers are used, they are most frequently chosen from amongst those which contain at least 20% of units as defined above, and preferably from amongst those which contain at least 50% of such units. The best results have been obtained with polymers which only contain units as defined above.

If the hydrophilic polymer is chosen from amongst the hydroxycarboxylated polymers, the latter can be used in the form of salts of polyhydroxycarboxylic acids or in the form of polyhydroxycarboxylic acids. In the latter case, they can be used in the form of the corresponding polylactones. Preferably, the hydroxycarboxylated polymers which can be used according to the invention are used in the form of polylactones. These polyhydroxycarboxylic acids can be lactonised to various extents. In general, polyhydroxycarboxylic acids in which more than 30% of the carboxyl groups are lactonised are used. Good results have been obtained with the polylactone derived from poly-alpha-hydroxyacrylic acid.

If the hydrophilic polymer present in the coating agent is a polyhydroxycarboxylic acid or the polylactone derived therefrom, a basic compound is also advantageously incorporated in the coating agent. The term basic compound is understood as denoting all the compounds which, when dissolved in water, are capable of imparting a pH of more than 7 thereto. Various types of basic compounds can be used for this purpose.

In general, compounds containing silicon atoms or phosphorus atoms are used. Examples of suitable basic compounds are alkali metal fluosilicates, silicates and phosphates. Good results have been obtained with sodium fluosilicate, sodium silicate and potassium silicate.

These basic compounds can be added in variable amounts. In general, they are used in proportions which are such that the weight ratio of the polylactone derived from the hydroxycarboxylated polymer to the basic compound is between 0.1 and 10 and most frequently between 0.2 and 5. Good results are obtained when the basic compound is present in the coating agent in an amount of 0.1 to 30% of the weight of the latter.

The hydrophilic polymer can be present in the coating agent in variable proportions. In general, it is present in an amount of 0.1 to 30% of the weight of the coating agent. Most frequently, the coating agent contains from 0.2 to 20% by weight of hydrophilic polymer.

The average molecular weight of the hydrophilic polymers present in the coating agent is more than about 300. It is generally between 2,000 and 1,000,000. The best results have been obtained when it is between about 5,000 and about 800,000.

The coating agent can also contain fillers of organic or mineral type. Mixtures of fillers can also be incorporated therein. The fillers are fine powders, the particle size of which is generally such that they pass through a sieve of 170 mesh and preferably 325 mesh (U.S. Standard). Fillers of organic type which are generally used are natural products based on cellulose, such as wood powder or peat flour. Fillers of organic or mineral type which are used are products based on silica, on silicates, on carbonates or on calcium salts. The fillers generally used are chosen from amongst ground or precipitated silica, ground sand, bentonite, talc, kaolin, diatomaceous earth, fuller's earth, vermiculite, clay, limestone, chalk, calcium carbonate, calcium oxide, calcium hydroxide, plaster and mixtures thereof. Some of these fillers are already present in the starting peroxide compound. This applies to the calcium salts in the case where the peroxide compound is calcium peroxide. Other non-phytotoxic fillers are also suitable. The proportion of fillers can vary within very wide limits. It is generally between 0 and 99% of the total weight of the coating agent and preferably between 0.1 and 99% of the total weight of the coating agent. Proportions of between 1 and 98% are suitable.

The coating agent can also contain one or more further additives such as adhesives other than the hydrophilic polymers of the invention, agents which make it possible to protect the seeds against the harmful effects of selective herbicides, fungicidal agents, disinfectants, nutrients (fertilisers), insecticides, agents capable of improving the germination and the quality of the products, and the like.

These additives can be present in variable proportions which can range up to 20% of the weight of the coating agent. The proportion of these other additives is generally between 0 and 10% of the weight of the coating agent.

Particularly advantageous coating agents can thus contain from 1 to 90% by weight of peroxide compounds, such as calcium peroxide, from 1 to 98% by weight of fillers, from 0 to 10% by weight of various additives and from 0.1 to 30% of at least one hydrophilic polymer chosen from amongst partially hydrolysed polyvinyl acetates, polyvinylpyrrolidone, alkylhydroxyalkylcelluloses, polymers consisting of the hydrolysed product resulting from the grafting of acrylonitrile onto starch, and mixtures of the polylactone derived from poly-alpha-hydroxyacrylic acid with basic compounds.

The total amount of coating agent used can vary within wide limits. In general, it is between 1 and 2,000% of the weight of the seeds to be coated, depending of the type of seeds, their shapes and their dimensions.

Coating can be carried out in accordance with various techniques. One particular technique consists in moistening the external surface of the seeds with water or an aqueous solution, in applying the solid coating agent to the seeds moistened in this way and in drying the coated seed.

The seeds can be moistened, for example, by spraying with water or an aqueous solution. If the seeds are sensitive to swelling in water, they are advantageously moistened with an aqueous solution containing an agent capable of limiting the swelling of the seeds.

These agents are generally chosen from amongst aldoses and basic compounds; certain hydrophilic polymers, like totally or partially hydrolysed polyvinyl esters, such as the products hydrolysed to an extent of less than 95%, can also perform this function. The nature of the agent which makes it possible to control the swelling of the seeds is chosen in accordance with the nature of the hydrophilic polymer present in the coating agent. If this hydrophilic polymer is a polylactone derived from a polyhydroxycarboxylic acid, a basic compound as defined above, and more particularly sodium fluosilicate or silicate, is generally chosen. If this hydrophilic polymer is a polymer derived from aldoses, a monomeric or oligomeric aldose, such as fructose, glucose or sucrose, or a polyvinyl ester hydrolysed to an extent of 40–90%, is generally chosen.

These aqueous solutions can contain variable amounts of agents capable of limiting the swelling of the seeds. In general, their concentration is relatively high and is equal to at least 3% of the weight of the solution. The maximum concentration of agent capable of limiting swelling corresponds to that of a saturated aqueous solution thereof.

The agents which make it possible to control the swelling of the seeds can be used in variable proportions which can range up to 20% of the weight of the coating agent.

The amount of water or of aqueous solution used to moisten the seeds can vary. In general, it is between 1 and 20% of the weight of the seeds.

The moistened seeds are treated with the mixture of coating constituents in various types of apparatuses which are in themselves known and which are suitable for agglomeration. Granulators, such as rotating plates, can thus be used. The coating agent is generally used in the form of a mixture of particles of small dimensions, preferably in the form of a powder. The average dimensions of the particles of solid coating agent are generally less than 100 microns.

Another technique consists in treating the seeds with an aqueous phase containing an agent capable of forming an impermeable film on the surface of the seed, and then, after the film has been formed, in coating the seeds with the solid coating agent. This technique is advantageously used for coating seeds of which the exocarp is particularly capable of very rapidly absorbing large amounts of water, such as leguminae seeds or poorly protected seeds such as maize and cruciferae (radish and the like).

These agents capable of forming an impermeable film are chosen from amongst the hydrophilic polymers of the invention and mixtures thereof. They are preferably chosen from amongst those which are capable of forming, on the surface of the seed, a film which is porous to gases but relatively non-porous to water, and more particularly a flexible film which is capable of contracting in the same proportions as the seed during the drying stage. They can be soluble or insoluble in water. If they are soluble in water, they are preferably chosen from amongst compounds having a low rate of dissolution in water.

Examples which may be mentioned of hydrophilic polymers which can be used to produce the impermeable film are totally or partially hydrolysed vinyl ester polymers, and more particularly those hydrolysed to an extent of less than 95%, and poly-alpha-hydroxyacrylic acids, their alkali metal and ammonium salts and the lactones derived therefrom. Good results have been obtained with polyvinyl acetates hydrolysed to an extent of 40-95%.

The weight of the films used according to the invention can vary within wide limits. In general, they are preferably used in small amounts and most frequently at a rate of 0.01 to 10% of the weight of the seeds to be treated. Good results have been obtained by using from 0.1 to 5%.

The films are advantageously obtained from a solution, an emulsion or an aqueous suspension. In general, aqueous mixtures containing at least 1% of solids, relative to the weight of the mixture, are used. Most frequently, this proportion is between 5 and 50%. The aqueous mixtures used according to the invention can contain constituents other than the essential constituent of the water-impermeable film, preferably at a rate of less than 5%, relative to the weight of the essential constituent.

The seeds can be treated with the aqueous mixture in various types of apparatuses which are in themselves known and which are suitable for coating. Granulators, such as rotary drums, rotating plates and the like, can thus be used. Preferably, after the treatment with the aqueous mixture, the seeds are dried and then subjected to actual coating. In general, they are dried sufficiently to reduce the residual moisture content of the seeds to a value which is equal to or close to the moisture content of the seeds before treatment. Good results have been obtained when the moisture content of the seeds covered with a water-impermeable film according to the invention does not exceed 130% by weight of the moisture content of the starting seeds. The drying of the seeds in accordance with the process of the invention is important. In fact, it enables the seeds, which have undergone swelling during the treatment, to return to their initial dimensions. The film constitutes a protection against the subsequent penetration, into the seeds, of certain products with which they are in contact during coating. Thus, it is possible to prevent the penetration, into the seed, of certain coating agents which possess some valuable properties (improvement in the germination, insecticidal power and the like), but which can have a phytotoxic effect if they penetrate into the seed itself. Penetration of water into the seed is thus also prevented and further swelling is avoided, with the result that better subsequent fixing of the coating agents is achieved, together with an improvement in adhesion and strength.

Drying can be carried out in accordance with any technique which is in itself known, such as passing an optionally heated, forced stream of air over the seeds, which can be arranged, for this purpose, in apparatuses such as sieves, or also drying by natural ventilation.

The seeds covered with a water-impermeable film are then coated with the coating agent of the invention, generally in an apparatus suitable for granulation.

This coating is generally carried out in the presence of an aqueous phase, which can be water or an aqueous solution and is more particularly a solution of the hydrophilic polymers of the invention. The coating agent itself is advantageously used in the form of a powder.

The seed-coating compositions comprise the coating agent and also, if appropriate, the agents capable of limiting the swelling of the seeds or the agents capable of forming an impermeable film. Examples of particularly suitable coating compositions are given below. If the seeds are treated with an aqueous phase containing agents capable of limiting the swelling of the seeds or agents capable of forming an impermeable film, the proportions used are taken into account in order to determine the total amounts of solid coating agent to be used for the granulation.

Composition I contains from 1 to 90% by weight of calcium peroxide, from 0.5 to 20% by weight of the polylactone derived from poly-alpha-hydroxyacrylic acid, from 0.5 to 30% by weight of basic compounds, such as sodium fluosilicate or sodium silicate or mixtures thereof, from 1 to 98% by weight of various fillers, such as calcium carbonate, oxide, hydroxide or sulphate, from 0 to 10% by weight of partially or totally hydrolysed polyvinyl esters and from 0 to 5% by weight of various additives.

Composition II contains from 1 to 90% by weight of calcium peroxide, from 0.1 to 10% by weight of polyvinyl esters hydrolysed to an extent of 40-90%, from 0 to 25% by weight of aldoses, such as sucrose or glucose, from 1 to 98% by weight of various fillers, such as calcium carbonate, oxide, hydroxide or sulphate, precipitated silica, kaolin or mixtures thereof, and from 0 to 5% by weight of various additives.

Composition III contains from 1 to 90% by weight of calcium peroxide, from 0.1 to 10% by weight of substituted or unsubstituted celluloses, such as alkylhydroxyalkylcelluloses, more particularly methylhydroxyethylcellulose or methylhydroxypropylcellulose, from 0 to 20% by weight of an agent for controlling the swelling of the seeds, such as glucose, sucrose or partially or totally hydrolysed polyvinyl esters, from 1 to 98% by weight of various fillers, such as calcium carbonate, oxide, hydroxide or sulphate, talc or mixtures thereof, and from 0 to 5% by weight of various additives.

Composition IV contains from 1 to 90% by weight of calcium peroxide, from 0.1 to 10% by weight of a polymer consisting of the hydrolysed product resulting from the grafting of acrylonitrile onto starch, from 0 to 20% by weight of an agent for controlling the swelling of the seeds, such as fructose, glucose, sucrose, totally or partially hydrolysed polyvinyl esters and basic compounds, more particularly sodium fluosilicate and silicate, from 1 to 98% by weight of various fillers, such as calcium carbonate, oxide, hydroxide or sulphate, talc, kaolin, silica, vermiculite or mixtures thereof, and from 0 to 5% of various additives.

Composition V contains from 1 to 90% by weight of calcium peroxide, from 0.1 to 15% by weight of polyvinylpyrrolidone, from 0 to 10% by weight of partially hydrolysed polyvinyl esters, from 1 to 98% by weight of various fillers, such as calcium carbonate, oxide, hydroxide or sulphate, talc, kaolin, silica, vermiculite or mixtures thereof, and from 0 to 5% by weight of various additives.

The invention can be applied to various types of seeds, such as leguminae, gramineae or dicotyledoneae seeds. In general, it is used for leguminae seeds such as the various kinds of peas, beans and lentils, lucerne, clover, vetch, soya, groundnut, field bean and lupin, gramineae seeds such as ray grass and cereals (maize, oats, rye, wheat, millet, sorghum, barley, rice and the like), dicotyledoneae seeds such as chicory, lettuce, tobacco, tomato, carrot, cabbages and rapeseed, and cruciferae seeds such as radish.

Some practical illustrative embodiments are given below in order to illustrate the invention without thereby restricting the scope thereof.

EXAMPLES 1 TO 14

Germination of pick peas

The technique consists in moistening pick pea seeds with an aqueous solution (composition a) at a rate of 10 ml of solution per 100 g of seeds.

The moist seeds are then treated in a granulator with a powdered coating agent (composition b).

Three powdered coating agents (composition b) were tested and their compositions are given below.

| Constituents | g/100 g |
|---|---|
| Powder F1 | |
| 80% pure calcium peroxide | 90 |
| Polylactone of poly-alpha-hydroxyacrylic acid | 5 |
| Na$_2$SiF$_6$ | 5 |
| Powder F2 | |
| 60% pure calcium peroxide | 60 |
| Hydrolysed product resulting from the grafting of acrylonitrile onto starch (H-SPAN) | 1.07 |
| Kaolin | 5.4 |
| Silica | 0.53 |
| Vermiculite | 10 |
| Talc | 23 |
| Powder F3 | |
| 60% pure calcium peroxide | 72.3 |
| Talc | 24.3 |
| Methylhydroxyethylcellulose | |

| Constituents | g/100 g |
|---|---|
| (2,000 cP) | 2.9 |

After coating, the seeds are slightly moistened with a small amount of water and are dried rapidly.

For germination, the coated seeds are placed either in a PETRI dish on moist filter paper (tests 1 to 10), or on moist sand (tests 11 to 14). The germination tests were carried out at 293–295 K.

The compositions used for coating and the results obtained are summarised in Tables I and II. Tests 1 and 11 were carried out without coating, by way of comparison. Test 2 was also carried out by way of comparison, using a coating agent only containing 58% pure calcium peroxide; the seeds had been moistened with demineralised water beforehand.

TABLE I

Coating of pick peas - Cultivation in a PETRI dish

| | Composition a | | Composition b | | | |
|---|---|---|---|---|---|---|
| Test No. | Solute | Concentration of the solution, % by weight | Type | Dose, g/100 g of seeds | Germination level, % | Germination time, days |
| 1 | — | | — | | 90 | 7 |
| 2 | — | | CaO$_2$ (58% pure) | 50 | 0 | — |
| 3 | polyvinyl acetate hydrolysed to an extent of 88% | 4 | F1 | 20 | 100 | 3–4 |
| 4 | Na$_2$SiF$_6$ | 5 | F1 | 20 | 100 | 3–4 |
| 5 | Na$_2$SiO$_3$ | 15 | F1 | 20 | 100 | 3–4 |
| 6 | polyvinyl acetate hydrolysed to an extent of 88% | 4 | F2 | 30 | 100 | 3–4 |
| 7 | sugar | 15 | F2 | 30 | 100 | 3 |
| 8 | Na$_2$SiF$_6$ | 5 | F2 | 30 | 100 | 3–4 |
| 9 | polyvinyl acetate hydrolysed to an extent of 88% | 4 | F3 | 30 | 90–100 | 4–5 |
| 10 | sugar | 15 | F3 | 30 | 90–100 | 4–5 |

TABLE II

Coating of pick peas - Cultivation on moist sand

| | Composition a | | Composition b | | |
|---|---|---|---|---|---|
| Test No. | Solute | Concentration of the solution, % by weight | Type | Dose, g/100 g of seeds | Germination time, days |
| 11 | — | | — | | 7 |
| 12 | Na$_2$SiF$_6$ | 5 | F1 | 20 | 4–5 |
| 13 | sugar | 15 | F2 | 30 | 4 |
| 14 | polyvinyl acetate hydroly- | 4 | F3 | 30 | 4–5 |

TABLE II-continued

Coating of pick peas - Cultivation on moist sand

| | Coating Composition a | | Composition b | | |
|---|---|---|---|---|---|
| Test No. | Solute | Concentration of the solution, % by weight | Type | Dose, g/100 g of seeds | Germination time, days |
| | sed to an extent of 88% | | | | |

In carrying out tests 12, 13 and 14, a marked fungicidal action due to the coating agent was found, compared with test 11 which was carried out without a coating agent. In tests 12 to 14, the subsequent growth of the roots was 3 times more rapid than in test 11. In test 12, the subsequent growth of the stems was twice as rapid as in test 11, and in tests 13 and 14, the growth of the stems was 3 times more rapid than in test 11.

EXAMPLES 15 TO 31

Germination of cereals

The technique is similar to that used for carrying out the above tests. To moisten the seeds before coating, they are treated with demineralised water at a rate of 10 ml of water per 100 g of seeds.

The powders F1 and F2 referred to above were used for coating wheat, barley and rice seeds. The compositions used for coating and the results obtained are summarised in Tables III (wheat), IV (barley) and V (rice).

Tests 19, 26 and 31 were carried out without coating, by way of comparison.

TABLE III

Coating of wheat

| | Coating Composition b | | Germination level, % | Germination time, days |
|---|---|---|---|---|
| Test No. | Type | Dose, g/100 g of seeds | | |
| 15 | F1 | 7.5 | 74 | 5 |
| 16 | F2 | 15 | 70 | 5 |
| 17 | F2 | 30 | 90 | 5 |
| 18 | F2 | 60 | 80 | 5 |
| 19 | — | — | 68 | 5 |

TABLE IV

Coating of barley

| | Coating Composition b | | Germination level, % | Germination time, days |
|---|---|---|---|---|
| Test No. | Type | Dose, g/100 g of seeds | | |
| 20 | F1 | 7.5 | 94 | 5 |
| 21 | F1 | 15 | 96 | 5 |
| 22 | F1 | 30 | 86 | 5 |
| 23 | F2 | 15 | 92 | 5 |
| 24 | F2 | 30 | 70 | 5 |
| 25 | F2 | 60 | 98 | 5 |
| 26 | — | — | 52 | 5 |

TABLE V

Coating of rice

| | Coating Composition b | | Germination level, % | Germination time, days |
|---|---|---|---|---|
| Test No. | Type | Dose, g/100 g of seeds | | |
| 27 | F1 | 30 | 96 | 5 |
| 28 | F2 | 15 | 100 | 5 |
| 29 | F2 | 30 | 94 | 5 |
| 30 | F2 | 60 | 98 | 5 |
| 31 | — | — | 94 | 5 |

EXAMPLE 32

Germination of rice

Rice seeds are moistened with an aqueous solution containing 0.6% of polyvinyl acetate hydrolysed to an extent of 88%, at a rate of 10 ml of solution per 100 g of seeds.

The moist seeds are treated in a granulator with 26 g of a powdered coating agent per 100 g of dry seeds.

The powdered coating agent has the following composition:

| Constituents | g/100 g |
|---|---|
| 80% pure calcium peroxide | 95 |
| Polyvinylpyrrolidone | 5 |

After coating, the seeds are slightly moistened with a small amount of water and are dried rapidly.

For germination, the coated seeds were placed in two pots having a side length of 22 cm and containing soil to a depth of 13 cm and water to a depth of 10 cm above the soil, thus flooding the crop.

25 seeds were deposited on the soil in each pot.

The pots are placed in a conditioned room, at 24° C. and 90% relative humidity, under an illumination of 10,000 lux for 12 hours per day.

Germination is observed after 35 days.

A control test was carried out with uncoated seeds. The results obtained are given in Table VI below.

TABLE VI

| | Germination level, % | | |
|---|---|---|---|
| | Batch 1 | Batch 2 | Average |
| Coated seeds | 68 | 96 | 82 |
| Uncoated seeds | 56 | 56 | 56 |

EXAMPLE 33

Germination of soya seeds

The soya seeds are moistened with a dilute aqueous solution containing 4% of polyvinyl acetate hydrolysed to an extent of 88%, of the MOWIOL 40-88 type sold by HOECHST, so as to obtain seeds covered with a film representing 0.24% by weight of this product.

For drying, the moist seeds are placed on a sieve through which dry air is passed until drying is complete.

The seeds are then treated in a granulator with calcium peroxide (containing 60% by weight of $CaO_2$, the remainder consisting of calcium oxide and hydroxide) at a rate of 12%, calculated in terms of pure $CaO_2$, and with the polylactone of poly-alpha-hydroxyacrylic acid at a rate of 10% of polylactone, relative to the weight of the seeds. During granulation, the seeds are uniformly moistened with a dilute aqueous solution containing 0.6% of MOWIOL 40-88.

After coating, the seeds are dried rapidly.

For germination, the seeds are placed in moist soil. The germination tests were carried out at about 20° C.

In all cases, the coating agent adheres very well to the seeds.

Comparison tests were carried out without treating the seeds with the solution of MOWIOL 40-88 beforehand, only coating as indicated above being carried out. In this case, a poor adhesion of the coating agent, which easily splits off, is observed.

Three batches of seeds were examined. The results obtained are summarised in Table VII below.

TABLE VII

|  | Germination level, % | | | |
| --- | --- | --- | --- | --- |
|  | Batch 1 | Batch 2 | Batch 3 | Average |
| Coating according to the invention | 100 | 60 | 100 | 87 |
| Comparison coating | 90 | 20 | 100 | 70 |

A further comparison test was carried out by subjecting the seeds to a treatment with polyvinyl acetate hydrolysed to an extent of 88%, followed by coating as described above, but without intermediate drying. A poor adhesion of the coating agent, which becomes brittle and splits off, is observed.

What is claimed is:

1. Process for the preparation of coated seeds, comprising: (a) treating the seeds with an aqueous phase which is selected from aqueous solutions containing an agent which is capable of limiting the swelling of the seeds and aqueous phases containing an agent which is capable of forming a water impermeable film on the surface of the seeds; (b) coating the treated seeds with a coating agent containing a peroxide compound and a hydrophilic polymer; and (c) drying the coated seeds.

2. Process according to claim 1, wherein the hydrophilic polymer is selected from the group consisting of polymers which possess a main chain containing carbon atoms which are directly or indirectly substituted by hydroxyl groups, —OH, carboxyl groups, —COO—, or carbamyl groups, —CON<.

3. Process according to claim 1 or 2, wherein the peroxide compound is calcium peroxide or magnesium peroxide.

4. Process according to claim 2, wherein the hydrophilic polymer is selected from the group consisting of polymers possessing a main chain which essentially consists of carbon atoms, the carbon atoms being directly or indirectly substituted by carboxyl groups, —COO—, or carbamyl groups, —CON<.

5. Process according to claim 4, wherein the hydrophilic polymer is selected from the group consisting of the hydrolysed products resulting from the grafting of acrylonitrile onto starch, polyvinylpyrrolidone, partially hydrolysed polyvinyl esters and poly-alpha-hydroxyacrylic acid and its derivatives.

6. Process according to claim 5, wherein the coating agent contains from 1 to 90% by weight of calcium peroxide, from 1 to 98% by weight of fillers, from 0 to 10% by weight of various additives and from 0.1 to 30% of at least one hydrophilic polymer selected from the group consisting of partially hydrolysed polyvinyl acetates, polyvinylpyrrolidone, alkylhydroxyalkylcelluloses, polymers consisting of the hydrolysed product resulting from the grafting of acrylonitrile onto starch, and mixtures of the polyactone derived from polyalphahydroxyacrylic acid with basic compounds.

7. Process according to claim 1 or 2, wherein the step of treating the seeds comprises moistening the seeds with said aqueous phase which is said solution which contains an agent for limiting the swelling of the seeds and the moistened seeds are brought directly into contact with the coating agent in the form of a powder, for coating the treated seeds.

8. Process according to claim 7, wherein said agent for limiting the swelling of the seeds is selected from the group consisting of partially hydrolysed polyvinyl esters, aldoses and basic compounds.

9. Process according to claims 1 or 2, wherein the step of treating the seeds comprises treating the seeds with said aqueous phase which contains an agent which is capable of forming a water impermeable film on the surface of the seeds, said agent which is capable of forming a water impermeable film on the surface of the seeds being a hydrophilic polymer, so as to cover the surface of the seeds with a water-impermeable film before coating the seeds with the coating agent.

10. Process according to claim 9, wherein the essential constituent of the film is a poly-alpha-hydroxyacrylic said derivative.

11. Process according to claim 9, wherein the essential constituent of the film is a polyvinyl ester having a hydrolysis level of 40-95%.

12. Process according to claim 9, wherein the seeds are dried after the treatment with the aqueous phase and before in step (a) but before the coating of step (b).

13. Process according to claim 2, wherein the hydrophilic polymer is selected from the group consisting of polymers possessing a main chain which consists essentially of carbon atoms and oxygen atoms, the carbon atoms being directly or indirectly substituted by carboxyl groups, —COO—, or carbamyl groups, —CON<.

14. Process according to claim 2, wherein the hydrophilic polymer is a polymer substituted by hydroxyl groups.

15. Process according to claim 14, wherein the hydrophilic polymer is selected from the group consisting of methylcellulose and carboxymethylcellulose.

16. Process according to claim 2, wherein the hydrophilic polymer is a composition containing a mixture of totally or partially hydrolyzed polyvinyl esters with carboxylated polymers.

17. Process according to claim 5, wherein the hydrophilic polymer is a partially hydrolyzed polyvinyl ester.

18. Process according to claim 17, wherein the hydrophilic polymer is a polyvinyl acetate in which 40 to 90% of the ester groups are hydrolyzed.

19. Process according to claim 5, wherein the hydrophilic polymer is polyvinylpyrrolidone.

20. Process according to claim 8, wherein the agent capable of limiting the swelling of the seeds is a totally or partially hydrolyzed polyvinyl ester.

21. Process according to claim 9, wherein the hydrophilic polymer contained in the aqueous phase is a polymer of totally or partially hydrolyzed vinyl esters.

* * * * *

UNITED STATES PATENT AND TRADEMARK OFFICE
CERTIFICATE OF CORRECTION

PATENT NO. : 4,344,979

DATED : August 17, 1982

INVENTOR(S) : Ignace Gago et al

It is certified that error appears in the above—identified patent and that said Letters Patent is hereby corrected as shown below:

```
          On the title page, before [51], insert
--[30]  Foreign Application Priority Data
        April 2, 1979 [FR] France..........79 08425
        January 11, 1980 [FR] France.......80 00773--.
```

Signed and Sealed this

Twenty-fifth Day of January 1983

[SEAL]

Attest:

GERALD J. MOSSINGHOFF

Attesting Officer  Commissioner of Patents and Trademarks